United States Patent [19]

Pieniak

[11] Patent Number: 4,723,954
[45] Date of Patent: Feb. 9, 1988

[54] WICKING FIBERS IN COMBINATION WITH A REPELLENT FABRIC

[75] Inventor: Heinz A. Pieniak, North Brunswick, N.J.

[73] Assignee: Personal Products Company, Milltown, N.J.

[21] Appl. No.: 828,073

[22] Filed: Jan. 31, 1986

Related U.S. Application Data

[63] Continuation of Ser. No. 628,127, Jul. 9, 1984, which is a continuation of Ser. No. 358,420, Mar. 11, 1982, which is a continuation-in-part of Ser. No. 153,377, May 27, 1980.

[51] Int. Cl.$^4$ ..................................................................
[52] U.S. Cl. .................................... 604/384; 604/378
[58] Field of Search ............... 604/366, 370, 378, 383, 604/384; 128/156

[56] References Cited

U.S. PATENT DOCUMENTS

| | | | |
|---|---|---|---|
| 3,285,245 | 11/1966 | Eldredge et al. | 128/156 |
| 3,965,904 | 6/1976 | Mesek et al. | 604/370 |
| 3,967,623 | 7/1976 | Butterworth et al. | 604/370 |
| 4,050,463 | 9/1977 | Schaar | 604/378 |
| 4,129,132 | 12/1978 | Butterworth et al. | 604/378 |

*Primary Examiner*—C. Fred Rosenbaum
*Assistant Examiner*—Sharon Rose
*Attorney, Agent, or Firm*—Lawrence D. Schuler

[57] ABSTRACT

The invention relates to the product and process for making an absorbent structure having a facing sheet and an absorbent batt in superposed relationship. The facing sheet is a nonwoven fabric. Some of the fibers of the batt extend into and are integral with the facing fabric. The extended fibers promote wicking of a liquid through the facing into the batt and stabilize the batt.

4 Claims, 7 Drawing Figures

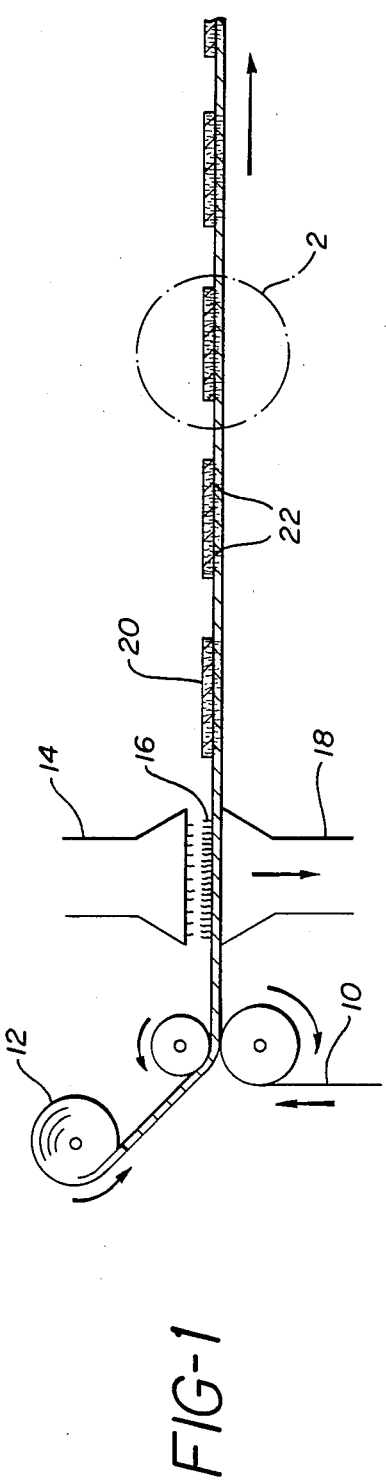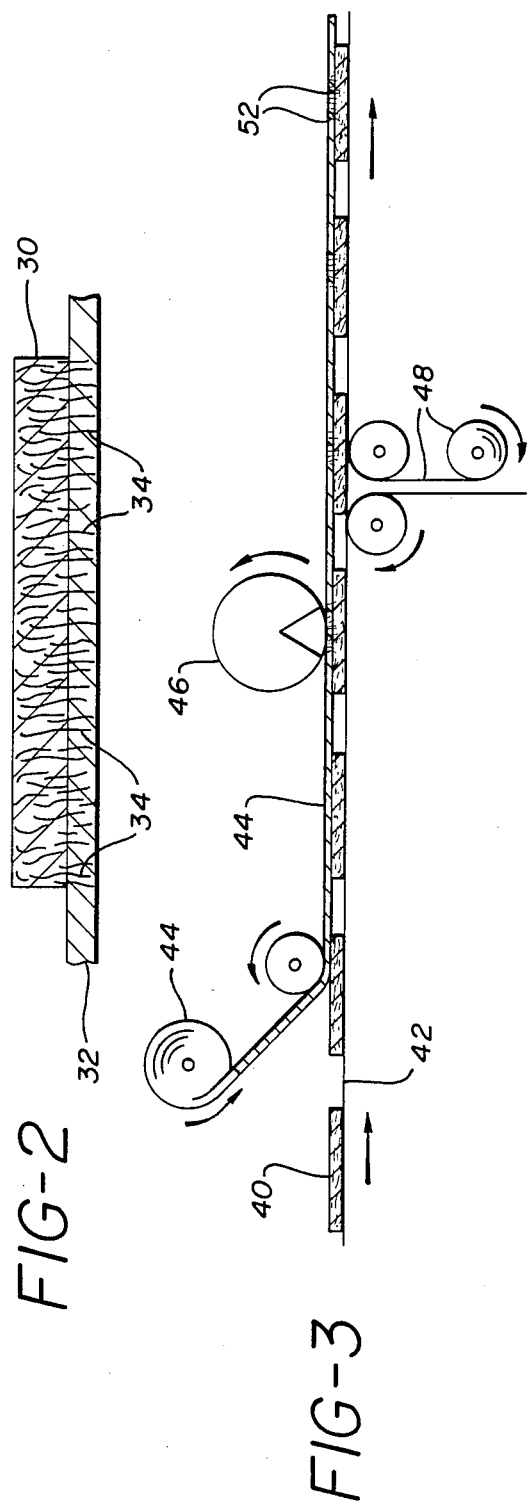

WICKING FIBERS IN COMBINATION WITH A REPELLENT FABRIC

This application is a continuation of application Ser. No. 628,127, filed 7/9/84, which is a continuation of application Ser. No. 358,420, filed 3/11/82, which is a continuation-in-part of application Ser. No. 153,377, filed 5/27/80.

BACKGROUND OF THE INVENTION

This invention relates to an absorbent structure having a water-repellent, nonwoven fabric facing in combination with wicking fibers in an absorbent batt.

Absorbent structures such as disposable diapers have been well accepted by consumers because they provide substantial advantages from the standpoint of convenience. Most disposable diapers incorporate three basic elements into their construction: a water-impervious backing sheet, a water-permeable facing sheet, and an absorbent batt situated between the facing sheet and the backing sheet.

One advantage which disposable diapers may have over non-disposable cloth diapers is that the multilayer disposable diaper, such as the one disclosed in U.S. Pat. No. 3,612,055 to Mesek et al, may be constructed so that when an infant voids into the diaper, the absorbent batt layer will absorb and retain the urine, while the facing sheet which is situated next to the infant's skin remains dry. To accomplish this result, the facing sheet must be less wettable than the absorbent batt. However, the facing sheet must be sufficiently wettable, as opposed to being water repellent, to permit the excreted body fluids to permeate through the facing sheet and into the absorbent layer behind it.

One method for construction of a facing sheet is from short length cellulosic fibers, such as wood pulp fibers or cotton linters or the like, as is disclosed in U.S. Pat. No. 3,633,348 to Loloia et al. Facing sheets so constructed are less expensive than woven fabrics, and thus are suitable for use in disposable diapers. The method of preparing this bonded nonwoven facing sheet includes the steps of forming a web of randomly laid dry fibers, impregnating the web with a binder and a surfactant, and drying the web to form the facing sheet. The surfactant is included in the steps of impregnating the web with the binder in order to offset the water-repellency which the binder imparts to the normally cellulosic fibers. The wettability of the nonwoven facing sheet can be controlled by the amount and placement of addition of a surfactant. However, as the wettability is increased, the water-repellency is decreased.

Another approach to the problem is the method disclosed in U.S. Pat. No. 3,730,184 to Mesek. In this method, a nonwoven facing sheet is prepared having a controlled degree of wettability in which the central portion of a web of randomly laid dry fibers is treated with a binder and a surfactant, while the marginal portions of the web are treated with binder material alone. In this manner the central portion is more wettable, whereas the surrounding portions are substantially water repellent.

Other absorbent structures, such as those used for absorbing body exudates, having a facing sheet and an absorbent batt, are catamenial devices, wound dressings, incontinence pads and the like.

It would be most desirable to provide a nonwoven facing sheet wherein the high water-repellency is retained and a means is provided for the liquid to penetrate the facing sheet to be absorbed by the absorbent panel below.

SUMMARY OF THE INVENTION

The present invention provides an absorbent structure having a facing sheet and an absorbent batt positioned in superposed relationship, the facing sheet, being of a nonwoven fabric which is substantially water-repellent, and having openings of a sufficient size so at least some fibers of the absorbent batt extend into and are integral with the facing fabric. The invention further provides a method for making the absorbent structure by forming the batt by air-laying the batt fibers onto the moisture-repellent nonwoven fabric facing while simultaneously applying suction to the opposite side of the fabric facing. Thus, some of the fibers from the absorbent batt extend into and become integral with the facing fabric.

The product and method of the present invention provides an inexpensive and convenient method for providing a means for penetration of a highly water-repellent facing fabric. The fibers integral with and extending into the facing fabric from the absorbent batt provide a wicking means for liquid to be transferred from the surface of the facing fabric into the absorbent batt.

BRIEF DESCRIPTION OF THE DRAWINGS

FIG. 1 is a schematic view illustrating the practice of one embodiment of the present invention;

FIG. 2 is a front elevational view illustrating one structure taken along lines 2—2 in FIG. 1;

FIG. 3 is a schematic view illustrating the practice of another embodiment of the present invention;

DETAILED DESCRIPTION

Figure 4:
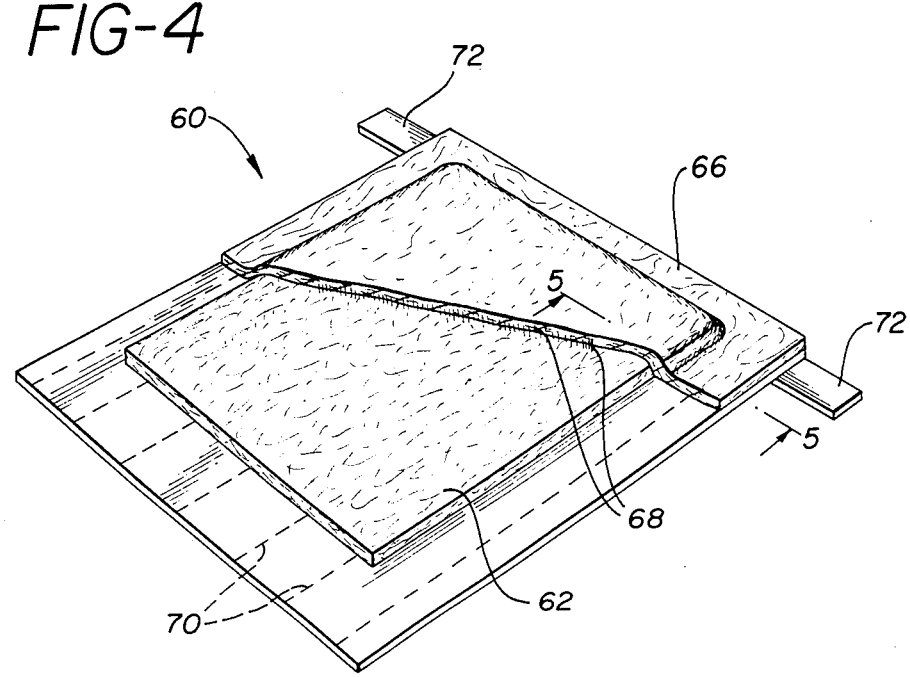
FIG. 4 is a perspective view illustrating one embodiment of the present invention.

Nonwoven fabrics which are suitable for use as facing sheets in disposable diapers, sanitary napkins, and similar absorbent products may be made of fibers which are predominantly short fibers or may be made from fibers which are staple fibers. The term "short fibers" is defined as wood pulp, cotton linters, or the like, where the fibers are less than 1¼ inches in length. In a typical fabric used for facing, the short fibers comprise about 75% to about 98% of the total fiber content of the nonwoven fabric, the balance being textile length fibers such as rayon.

Nonwoven fabrics made from textile length staple fibers include polyester, polypropylene, polyethylene, rayon and the like. In both instances, the fibers are air-laid and then bonded to form the fabric.

Entangled fiber fabrics and spun-bonded nonwoven fabrics are also suitable, as well as heat-bonded or melt-bonded fabrics.

Typical facing sheet materials have fabric weights in the range of about 0.5 to 3 oz./sq. yd. and densities of less than 0.15 gm/cc. The dry strength of the facing sheet for a fabric having a weight of about 1.5 oz./sq. yd. is at least 0.15 lb./inch of width in the machine direction, and at least 0.1 lb./inch of width in the cross direction. Such fabrics have unusually good elongation, loft, softness, and drape characteristics.

Fabrics of this general type are prepared by first forming a web of randomly laid dry fibers. The web is then impregnated with a binder by flowing a solution or dispersion of the binder through the web. The impregnated web is then subjected to suction to remove excess binder and assure uniform distribution of binder throughout the fiber web. The web so formed is then dried and heated to cure the binder. The resulting web is a suitable fabric for use as a facing, being substantially water-repellent. Suitable binders include the self-curing acrylic latex family, the urethane family, and other binders known in the art. A typical method of manufacturing bonded, nonwoven fabrics is shown in U.S. Pat. No. 3,663,348 to Liloia et al.

The absorbent batt comprises a batt of short fibers, generally wood pulp fibers of a length less than about ¼ inch. The batt preferably is formed by air-laying of the fibers on a foraminous surface such as the nonwoven facing to the desired thickness. Shortly after the fibers are deposited on the foraminous surface, they are subjected to light compression or vacuum to form a loosely compacted fibrous absorbent batt comprised preferably of wood pulp fibers. It is some of the fibers from this batt that extend into and become integral with the facing fabric to provide a wicking means for liquid to be transferred from the surface of the facing fabric into the absorbent batt. Referring now to the drawings, FIG. 1 represents a schematic diagram of a method of preparing the absorbent structure of the present invention. A foraminous support 10 moving continuously in one direction is provided. The nonwoven facing fabric 12 is laid on top of the foraminous support, also moving in the same direction at the same speed. Fibers 16 to form the absorbent batt are air-laid by an air-laying machine such as a hammermill or a dual rotor 14, and laid on the surface of the facing fabric. A suction box 18 is located immediately below the area upon which the fibers are laid, creating a vacuum in a downward direction. The fibers are laid in a prescribed design to a predetermined thickness. After the air-laying step, the absorbent structure 20 continues on the foraminous support and is subsequently placed into the final product. Fibers 22 are shown as penetrating the surface and extending substantially through the facing fabric 12. FIG. 2 is an exploded view of a typical absorbent structure 30 showing the wicking fibers 34 extending into and substantially through the facing fabric 32.

FIG. 3 depicts yet another method of preparing the absorbent structure of the present invention. An absorbent batt 40 is preformed in the desired shape and thickness on a foraminous support 42 which is continuously conveyed in a given direction. Over the surface of the absorbent batt, the facing fabric 44 is laid and is continuously conveyed at the same speed as the foraminous support. At a predetermined point, a vacuum drum 46, or like mechanism, creates a suction in a predetermined pattern over the absorbent batt, drawing fibers 52 into the facing fabric 44. When preparing an absorbent structure such as a disposable diaper, a moisture-impermeable sheet 48, such as polyethylene, is placed under the absorbent structure so as to provide a layered laminate. The laminate then continues through assembly stations to form the final product.

In FIG. 4 a typical diaper structure 60 is shown. The moisture-impermeable backing sheet 62 extends beyond the margins of the absorbent batt 64 and is substantially the same size as the facing sheet 66. Fibers 68 extend from the absorbent batt 64 and substantially penetrate the facing sheet 66. The diaper structure is laminated by glue lines 70. Tape tabs 72 are provided to secure the diaper structure about the infant.

Figure 5:
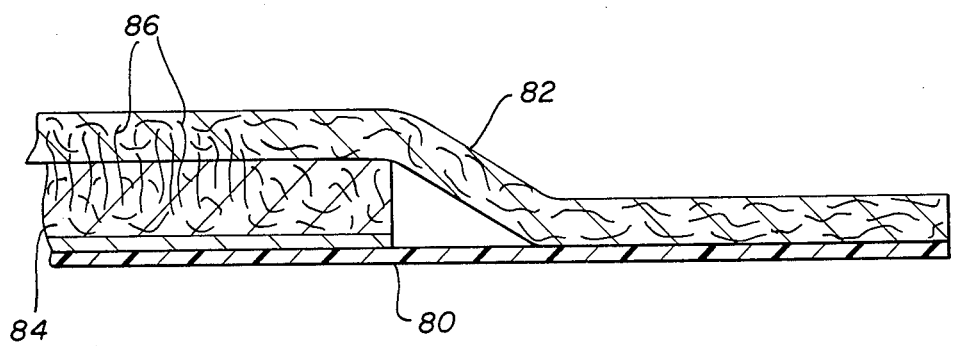
FIG. 5 is an enlarged cross-sectional view through lines 5—5 of FIG. 4.

FIG. 5 is an exploded partial view of a cross-section of the diaper 60 in FIG. 4. The backing sheet 80 is laminated to the facing fabric 82 and to the absorbent batt 84. Fibers 86 from the absorbent batt 84 substantially penetrate the facing fabric 82.

Figure 6:
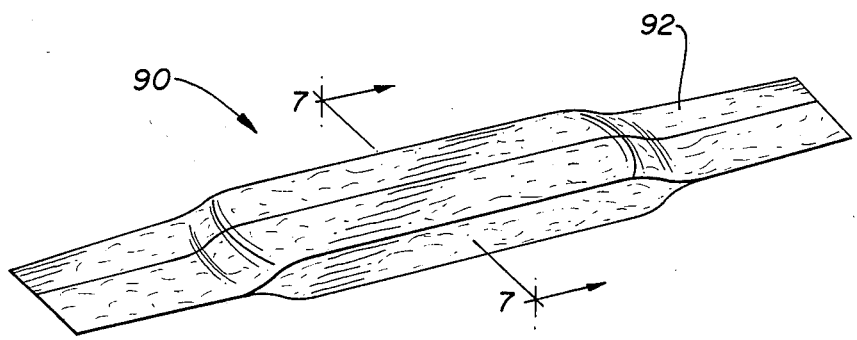
FIG. 6 is a perspective view of a catamenial napkin embodying the present invention.
Figure 7:
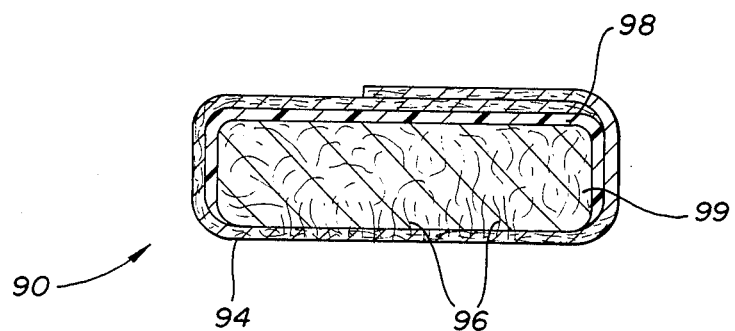
FIG. 7 is a cross-sectional view of the sanitary napkin of FIG. 6 taken along line 7—7.

FIG. 6 depicts a typical sanitary napkin 90 encompassing the absorbent structure of the present invention. The facing fabric 92 surrounds the absorbent batt and the moisture-impermeable sheet material which encompasses part of the napkin. FIG. 7 depicts a cross-sectional view of the napkin 90 of FIG. 6 at lines 7—7. An absorbent batt 99 is partially surrounded by a moisture-impermeable sheet 98. The entire structure is then wrapped in the facing fabric 94 having integral therewith fibers 96 in the functional areas of the absorbent batt 99.

It has been found that the fibers extending into and integral with the facing fabric promote wicking of liquid from the exterior of the facing fabric into the absorbent batt in the absorbent structure of the present invention. These wicking fibers permit retention of high water-repellency of the facing fabric so that as moisture is drawn into the absorbent batt, the moisture does not have a tendency to leak back through the facing fabric, keeping the wearer of the absorbent structure dry. It is equally important that the penetration time of the liquid through the fabric to the absorbent batt be very rapid. The faster the penetration time of the liquid through the fabric, the less opportunity there is for the fabric to absorb the liquid, thus giving the fabric a drier feel.

Another advantage of the present invention is the ease with which a pattern of wicking fibers can be provided. For instance, the void zone of a disposable diaper is a central region which is known. It is advantageous, therefore, to provide wicking fibers only in the void zone. Thus the surrounding areas of the facing sheet retain all of the water-repellent characteristics thus providing a "containerized" structure which has very little leakage, if any.

The same is true for a sanitary napkin. For instance, commercial products use a silicone spray on the sides and along the side margins of the facing sheet to attempt to prevent leakage. However, the ends of the facing sheet remain unprotected because it is difficult to spray silicone in a cross-machine direction. In the instance of the present invention, the entire facing sheet can be made water-repellent and then only the void zone is water-permeable, thus providing a containerized product.

The following examples illustrate the present invention. They are presented for illustrative purposes only, and should not be construed as limiting the invention in any way.

EXAMPLE 1

A nonwoven fabric which is 100% polyester of reduced aperture size wherein the apertures are not distinct, is conveyed on a screen below a defibrating mill. Wood pulp is defibrated and the wood pulp fibers in the form of fluff are air-laid onto the polyester fabric.

Beneath the screen in the region where the fibers are laid is a vacuum box which applies suction to a portion of the under surface of the fabric. Sufficient vacuum force is used to cause those fibers which enter the surface of the nonwoven fabric to substantially penetrate the fabric to the other surface. The fluff is laid on the fabric in rectangular shapes having a thickness of about 0.3 inch. The resulting absorbent structures are separated into individual units and are tested in the following manner:

The absorbent structure is laid on a flat level surface with the fabric side up. A pressure plate is placed on a portion of the structure. The pressure plate is a bronze metal plate 3×4 inches with a smooth flat bottom surface and a smooth tapered hole, ¾ inch in diameter, in the center. The plate weighs 300 grams.

A solution (1.59% saline) in the amount of 5 ml. is drained into the corner formed by the plate rim and tapered plate walls by means of a pipette. A stopwatch is started when the solution contacts the fabric and stopped where there is no pool of liquid on any part of the fabric. If the solution penetrates the fabric the instant it makes contact, the penetration time is termed "instantaneous".

Several control samples are prepared by placing the fabric on the absorbent batt. In each instance the time elapsed is greater than 8 minutes. Five samples are tested and have the following times:

Samples (1) 50 seconds
(2) 50 seconds
(3) 4 minutes 43 seconds
(4) 1 minute 8 seconds
(5) 1 minute Fifteen samples of a non-apertured 100% polyester fabric (0.8 oz./sq. yd.) are prepared by depositing pulp fibers on the fabric in the presence of vacuum. Each of the 15 samples is penetrated by the saline solution instantaneously.

EXAMPLE 2

Fabric made from short length cellulosic fibers, as shown in U.S. Pat. No. 3,633,348, is rendered water-repellent and is conveyed on a screen whereupon defibrated wood pulp fibers are deposited on the fabric as described in Example 1. Vacuum is applied to the fabric side of the absorbent structure. The structures are separated and the plate test described above is conducted.

The control samples are prepared by laying the fabric on a fluff panel. These structures are then tested in the same manner.

|    | Control              | Invention Structure |
|----|----------------------|---------------------|
| A. | 1 minute 35 seconds  | (6) 53 seconds      |
| B. | 1 minute 14 seconds  | (7) 46 seconds      |
| C. | 55 seconds           | (8) 42 seconds      |
| D. | 1 minute 2 seconds   | (9) 33 seconds      |
| E. | 1 minute 17 seconds  | (10) 50 seconds     |
| F. | 1 minute 18 seconds  | (11) 31 seconds     |
| G. | 43 seconds           | (12) 36 seconds     |

|    | Control             | Invention Structure |
|----|---------------------|---------------------|
| H. | 1 minute 17 seconds | (13) 39 seconds     |
|    |                     | (14) 41 seconds     |

EXAMPLE 3

Pulp fluff is deposited onto 100% polyester nonwoven fabric at a speed of 60 ft./min. using a hammermill. As the pulp is deposited, vacuum below the mill head is applied to the central portion of the pulp fluff batt. Each batt weighs about 30 grams. Samples are taken from various places in the central portion of each batt and tested according to the above procedure.

The control samples are formed by placing the same fabric onto a preformed pulp batt.

The liquid penetration times are as follows:

|    | Control Samples | Invention Samples |
|----|-----------------|-------------------|
| I. | >5 minutes      | (15) 4 seconds    |
| J. | 8 seconds       | (16) 2 seconds    |
| K. | 1 minute 12 seconds | (17) 1 second |
| L. | >5 minutes      | (18) 9 seconds    |
| M. | 25 seconds      | (19) 7 seconds    |
| N. | 45 seconds      | (20) 5 seconds    |
| O. | 24 seconds      | (21) 5 seconds    |
| P. | >5 minutes      | (22) 2 seconds    |
| Q. | >5 minutes      | (23) 2 seconds    |
| R. | >5 minutes      | (24) 3 seconds    |
| S. | >5 minutes      |                   |

The results shown above clearly show that liquid penetration and wicking times are substantially reduced when the absorbent structure of the present invention is utilized. The faster liquid penetrates a fabric the drier the fabric remains. Thus when used in a product such as a diaper or sanitary napkin, the surface of the fabric against the wearer stays drier.

Furthermore, a high degree of repellency may be retained by a fabric, thus preventing liquid from striking back through the fabric.

From the foregoing, it will be observed that numerous variations and modifications may be effected without departing from the true spirit and scope of the novel concept of this invention.

I claim:

1. An absorbent structure comprising a separate facing sheet and an absorbent batt of loosely-compacted cellulosic fibers positioned in superposed relationship to the separate facing sheet, the facing sheet being a substantially water-repellent nonwoven fabric consisting essentially of textile length, staple fibers selected from the group consisting of polyester, polyethylene, polypropylene, and rayon fibers and having at least some fibers from the absorbent batt pulled by suction into and becoming integral with the facing fabric.

2. The absorbent structure of claim 1 wherein the suction is applied in a prescribed pattern.

3. A disposable diaper containing as its absorbent layer the absorbent structure of claim 1.

4. A sanitary napkin containing as the absorbent layer the absorbent structure of claim 1.

* * * * *